US010799521B2

(12) United States Patent
Zhao et al.

(10) Patent No.: US 10,799,521 B2
(45) Date of Patent: *Oct. 13, 2020

(54) USE OF ICARITIN IN PREPARING MEDICAMENT FOR PREVENTING OR TREATING HEMATOCYTOPENIA

(71) Applicant: Lunan Pharmaceutical Group Corporation, Linyi, Shandong Province (CN)

(72) Inventors: Zhiquan Zhao, Linyi (CN); Jingchun Yao, Linyi (CN); Xin Li, Linyi (CN); Yongxia Guan, Linyi (CN); Guangyan Li, Linyi (CN)

(73) Assignee: LUNAN PHARMACEUTICAL GROUP CORPORATION, Linyi (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/724,573

(22) Filed: Dec. 23, 2019

(65) Prior Publication Data

US 2020/0147115 A1   May 14, 2020

Related U.S. Application Data

(63) Continuation of application No. 15/030,671, filed as application No. PCT/CN2014/088944 on Oct. 20, 2014, now Pat. No. 10,555,962.

(30) Foreign Application Priority Data

Oct. 21, 2013  (CN) .......................... 2013 1 0493718
Dec. 4, 2013   (CN) .......................... 2013 1 0646101

(51) Int. Cl.

| A61K 31/7048 | (2006.01) |
|---|---|
| A61K 31/352 | (2006.01) |
| A61K 9/00 | (2006.01) |
| A61K 9/107 | (2006.01) |
| A61K 9/16 | (2006.01) |
| A61K 9/20 | (2006.01) |
| A61K 9/48 | (2006.01) |
| A61K 45/06 | (2006.01) |

(52) U.S. Cl.
CPC ........ *A61K 31/7048* (2013.01); *A61K 9/0019* (2013.01); *A61K 9/1075* (2013.01); *A61K 9/16* (2013.01); *A61K 9/20* (2013.01); *A61K 9/48* (2013.01); *A61K 31/352* (2013.01); *A61K 45/06* (2013.01)

(58) Field of Classification Search
CPC ................................................. A61K 31/7048
See application file for complete search history.

(56) References Cited

U.S. PATENT DOCUMENTS

| 6,399,579 | B1 | 6/2002 | Lenoble et al. | |
|---|---|---|---|---|
| 10,555,962 | B2 * | 2/2020 | Zhao ................... | A61K 31/352 |
| 2004/0072824 | A1 | 4/2004 | Telerman | |
| 2006/0069064 | A1 | 3/2006 | Khaldoyanidi | |

FOREIGN PATENT DOCUMENTS

| CN | 1460482 A | 12/2003 |
|---|---|---|
| CN | 101637467 A | 2/2010 |
| EP | 2 626 071 A1 | 8/2013 |
| EP | 2 808 016 A1 | 12/2014 |
| GB | 1093293 | 11/1967 |
| WO | 2015/112898 A1 | 7/2015 |

OTHER PUBLICATIONS

Yuan et al., "Research progress of phytoestrogens-like chemical constituents in natural medicines", China Journal of : Chinese Materia Medics, vol. 39, Issue 23, Dec. 2014, pp. 1-6 {English abstract on p. 6).
Vanhees et al., "Epigenetics: prenatal exposure to genistein leaves a permanent signature on the hematopoietic ineage", The FASEB Journal, vol. 25, Feb. 2011, pp. 797-807.
Todaka et al., "Fetal exposure to phytoestrogens—The difference in phytoestrogen status between mother and fetus", Environmental Research 99, 2005, pp. 195-203.
Mathijssen et al., "Effects of St. John's Wort on Irinotecan Metabolism", Brief Communications, Journal of the National Cancer Institute, vol. 94, No. 16, Aug. 1, 2002, pp. 1247-1249.
Reif et al., "Effect of grapefruit juice intake on etoposide bioavailability", European Journal Clinical Pharmacol, vol. 58, 2002, pp. 491-494.
Chiang et al., "Life-threatening interaction between the root extract of Pueraria lobata and methotrexate in rats", Toxicology and Applied Pharmacology, vol. 209, 2005, pp. 263-268.
Kim et al., "Reversal of—glycoprotein-mediated multidrug resistance by ginsenoside Rg3", Biochemical Pharmacology, vol. 65, 2003, pp. 75-82.
Sugimachi et al, "Postoperative chemo-endocrine treatment . . . ", 1999, vol. 56, pp. 113-124, Full copy attached.
English translation of priority document CN 201310646101.1 filed Dec. 4, 2013.
English translation of priority document CN 201310493718.4 filed Oct. 21, 2013.
Sugimachi et al., Postoperative chemo-endocrine treatment with mitomycin C, tamoxifen, and UFT is effective for patients with premenopausal estrogen receptor positive stage II breast cancer, 1999, Breast Cancer Research and Treatment, vol. 56 (2), pp. 113-124, Abstract only.
Lou et al., CN 1460482, STN entry (w/ English abstract), machine translation, and original document in Chinese, 20 pages.

(Continued)

*Primary Examiner* — Rei Tsang Shiao
(74) *Attorney, Agent, or Firm* — Renner, Otto, Boisselle & Sklar, LLP

(57) ABSTRACT

The present application relates to a method of icaritin in preventing or treating hematocytopenia. Particularly, icaritin may be used to prevent or treat bone marrow suppression caused by chemotherapeutic drugs, and may also be used to prevent or treat thrombocytopenia, for example, immune thrombocytopenia.

12 Claims, No Drawings

(56) References Cited

OTHER PUBLICATIONS

Extended European Search Report received in corresponding Application No. 14855388.6 dated Apr. 3, 2017.
Database WPI, Week 200420, Thomson Scientific, London, GB, XP-002768535, Lou et al., "Medicine composite :: containing icaritin and demethylicaritin and its application".
Zhu et al., "Icaritin Shows Potent Anti-Leukemia Activity on Chronic Myeloid Leukemia In Vitro and In Vivo by Regulating MAPK/ERK/JNK and JAK2/STAT3 /AKT Signalings", PLoS ONE, vol. 6, Issue 8, Aug. 2011, pp. 1-11.
Li et al., "Icaritin induces AML cell apoptosis via the MAPK/ERK and PI3K/AKT signal pathways", International Journal Uf Hematology, vol. 97, No. 5, Apr. 3, 2013, pp. 617-623.
International Search Report for corresponding International Application No. PCT/CN2014/088944 dated Feb. 6, 2015.
Ge et al., "The effect of icarrin (ICA) on the hematopoietic regulation in mice after radiation", China J Cancer Prev Treat, vol. 10, No. 7, Jul. 31, 2003, pp. 687 and 688.
Zhao et al., "The effect of ICA on the cell-immunosuppressive and bone-marrow-suppressive mice after :; hemotherapy", Chinese Journal of Cellular and Molecular Immunology, vol. 10, No. 26, Oct. 18, 2010, pp. 976-979.

\* cited by examiner ically common disease characterized by coagulation disorders and bleeding or more severely hemorrhoea and life-threatening, and represents about 30% of clinical hemorrhagic diseases.

USE OF ICARITIN IN PREPARING MEDICAMENT FOR PREVENTING OR TREATING HEMATOCYTOPENIA

This application is a continuation of U.S. application Ser. No. 15/030,671 filed Apr. 20, 2016, which is a national phase of International Application No. PCT/CN2014/088944 filed Oct. 20, 2014, which claims priority to Application Nos. CN 201310493718.4 filed Oct. 21, 2013 and CN 201310646101.1 filed Dec. 4, 2013.

TECHNICAL FIELD

The present application relates to medical use of icaritin, in particularly use thereof in preparing a medicament for preventing or treating hematocytopenia.

BACKGROUND ART

Normal blood comprises a great number of cells, including oxygen-carrying red blood cells and infection-fighting white blood cells. White blood cells include neutrophils, eosinophils and basophils. White blood cells are produced by the hematopoiesis of bone marrow. Normal blood further comprises platelets. Platelets are tiny cell fragments which induce blood coagulation. Blood cells in human body are produced by the hematopoietic system. The hematopoietic system in human body is comprised of a small amount of bone marrow hematopoietic stem cells and different series of hematopoietic cells at different development stages, and is very sensitive to hazardous factors produced by various physical-chemical processes and in vivo metabolism, such as body fatigue, exposure to radiation or certain chemotherapeutic drugs, etc., which may cause diseases such as hematocytopenia induced anemia, bone marrow suppression, etc. In addition, there is also primary hematocytopenia, such as primary thrombocytopenic purpura, etc.

Cancer patients have to receive treatments mainly involving radiotherapy and chemotherapy over a relatively long period of time. Radiotherapy and chemotherapy are therapies in which radiation and cytotoxic agents are used to treat cancers. However, radiotherapy and most of chemotherapy are non-specific, and are toxic to normal and rapidly-dividing cells. High-dose radiation is also toxic to normal and rapidly-dividing cells. This often results in various side effects in patients receiving chemotherapy and radiotherapy. While other normal tissues may also be adversely affected, bone marrow is particularly sensitive to such proliferation-specific treatments as chemotherapy or radiotherapy. Bone marrow suppression, i.e. reduction in the production of blood cells in bone marrow, is one of such side effects. This is reflected by reduction in the proliferation function of the bone marrow, reduction in blood cell count, reduction in peripheral blood leukocytes, reduction in neutrophils, and/or thrombocytopenia, or even aplastic anemia, which severely affects the survival quality of patients or is even life-threatening.

Clinically, patients receiving radiotherapy or chemotherapy are highly susceptible to damages and suffer different degrees of bone marrow suppression. This is reflected by reduction in the number of peripheral blood leukocytes, reduction in the number of neutrophils and/or thrombocytopenia. In the peripheral blood of human body, neutrophils represent about 50-70% of the total number of white blood cells, and the increase and decrease thereof directly affect the change in the total number of white blood cells. That is, white blood cells increase with the increase of neutrophils; and the total number of white blood cells reduces with the reduction of neutrophils. The correlation between the two numbers also represents in the consistency in their significances, i.e. the significance of the increase and decrease of neutrophils is substantially same as that of the increase and decrease of the total number of white blood cells. Patients at bone marrow suppression state are susceptible to infections. Deficiencies in neutrophils and platelets are main reasons for the morbidity and mortality after cancer treatment and result in high cost in cancer treatment.

However, radiotherapy and chemotherapy are currently still the most commonly used means in the treatment of tumors. Complications such as bone marrow hematopoietic suppression and the like induced by radiotherapy and chemotherapy have become important factors affecting the survival quality of patients. Some chemical drugs having explicit efficacy in assisting tumor treatment would cause many adverse effects after use by themselves, which would add the pain of patients. Many medical practitioners are making efforts to seek drugs which are effective and show fewer side effects to combat the damages caused by radiotherapy and chemotherapy.

In current clinical treatment of bone marrow suppression, a variety of growth factors are usually administered to increase the proliferation of hematopoietic cells. Gene recombined hematopoietic growth factors which are marketed in recent years, such as leucomax (rhGM-GSF), filgrastim (rhG-CSF), and the like, are significant when used to increase white blood cells. However, they are expensive and not affordable for most patients. In addition, rhGM-GSF and rhG-CSF neither can be used simultaneously with chemotherapy, nor can be used prophylactically, and only can be administered when leukocytopenia occurs; otherwise toxic side effects would be generated. In addition, gene therapies using hematopoietic growth factors, such as IL-6, IL-3, etc., are still in the stage of animal tests. On the other hand, autologous bone marrow transplant is often used in combination with high-dose chemotherapy, and is difficult to be repeatedly applied. Therefore, finding a safe, effective and inexpensive method to prevent and treat hematocytopenia, in particular that resulted from the side effects of chemotherapy and radiotherapy, and increase the number of white blood cells after chemotherapy and radiotherapy would be very significant for improving the efficacy of chemotherapy and radiotherapy of tumors, prolonging the surviving time and improving the surviving quality of cancer patients.

Thrombocytopenia is a disease in which the reduction of platelets in the peripheral blood causes bleeding of skin mucosa and internal organs, which is mainly manifested by spontaneous skin petechiae and ecchymosis, mucosal bleeding, epistaxis and gum bleeding, occurrence of purple blisters in oral mucosa and tongue, etc. It is a clinically common disease characterized by coagulation disorders and bleeding or more severely hemorrhoea and life-threatening, and represents about 30% of clinical hemorrhagic diseases.

The causes for thrombocytopenia may be divided into: (1) Reduction in production or inefficiency and death of platelets: including inherited and acquired ones. Acquired reduction in platelet production is due to certain factors, such as drug, malignant tumor, infection, ionizing radiation, etc., which damage hematopoietic stem cells or interfere with their proliferation in the bone marrow. It may affect various hematopoietic cell systems, and is commonly accompanying with different degrees of anemia, leukopenia, and significant reduction in bone marrow megakaryocytes. (2) Excessive destruction of platelets: including congenital and acquired ones. Acquired excessive destruction of platelets includes immune and non-immune ones. Common immune excessive destruction of platelets includes idiopathic thrombocytopenic purpura and drug-induced thrombocytopenia. Non-immune excessive destruction of platelets includes infections, disseminated intravascular coagulation, thrombotic thrombocytopenic purpura, etc. (3) Excessive retention of platelets in spleen: the most common example is spleen hyperfunction.

The nosogenesis of thrombocytopenia includes the followings: 1) Immune factors: clinically including thrombocytopenia induced by immune diseases such as severe liver disease, lupus erythematosus, idiopathic thrombocytopenic purpura, etc., in which antibodies damage the platelets; 2) Infectious factors: the common factors causing thrombocytopenia, bacterial and viral infections can directly damage hematopoietic cells, and reduce platelet growth. Acute attack stage of aplastic anemia, acute leukemia, or the like, is often accompanied by severe infection and tendency of bleeding, such as petechiae or erythema on the skin, or nasal bleeding with unknown cause, etc; 3) Drug-related factors: certain drugs may cause the reduction in the platelet count in the peripheral blood, which results in hemorrhagic diseases; and 4) Platelet dysfunction: such as thrombasthenia, Bernard-Soulier syndrome, etc.

Clinically most common thrombocytopenia includes immune thrombocytopenic purpura (ITP) and thrombotic thrombocytopenic purpura (TTP), in which ITP is clinically the most common cause of thrombocytopenia. ITP has long been considered as a hemorrhagic disease caused by thrombocytopenia with unknown causes, and therefore referred to as primary or idiopathic thrombocytopenic purpura. It was later discovered that there are autoantibodies in ITP patients, which identify platelet autoantigens. The binding of autoantibody with platelet antigen shortens the life span of platelets, increases the damage and reduces the number of platelets, indicating that this disease is a hemorrhagic disease associated with immune response.

In clinic, immune thrombocytopenic purpura (ITP) is a relatively common hemorrhagic disease, and may occur at any age stage with an estimated ITP incidence rate of population being 1/10000. It is usually acute in children, and chronic in adults, and usually occurs in children and young adults. The clinical manifestations thereof include skin petechiae and ecchymosis, bleeding in skin mucous, while critically ill patients may suffer from joint pain or abdominal pain, hemafecia, hematemesis, collapse, or the like. More severely, it may develop into purpura nephritis. Primary thrombocytopenic purpura is an immune syndrome and a common hemorrhagic disease, characterized by the presence of anti-platelet antibodies in the blood circulation, which destruct the platelets excessively and cause purpura; and by normal or increased megakaryocytes in bone marrow, and immaturation.

To date, the first choice in treating thrombocytopenic purpura by western medicine is adrenal cortex hormone. Although hormone can increase platelets, but once the hormone is administered at a reduced dose or is discontinued, platelets would reduce again. Frequent use of the hormone would lead significant side effects to human body, and would result in diseases such as central obesity, hypertension and diabetes during the treatment. Other treatments, such as infusion of platelets, spleen resection, and the like, have disadvantages such as increased infection rates, causing active peptic ulcer, bleeding, reduced immune function, hyperglycosemia, or the like, worsened symptoms after drug discontinuance, and non-persistent efficacy. When conventional therapies such as immunosuppressants and spleen resection are employed, the disease cannot be eradicated in many patients due to hormone withdrawal syndrome as a result of the contraindication and side effects of hormones. In addition, immunosuppressants cannot be widely used due to significant toxic side effects, relapse after drug discontinuance, and risks of bone marrow suppression and induced tumors. In recent years, new therapies such as high-dose gamma globulin impact and plasma replacement keep emerging, but there still lacks fundamental therapeutic measures.

*Epimedium* refers to dry stems and leaves of the plant, *Epimedium brevicornum* Maxim., *Epimedium sagittatum* Maxim., *Epimedium pubescens* Maxim, or *Epimedium koreanum* Nakai, in the family Berberidaceae and is mainly used in clinic for treating deficiency of kidney yang, impotence and frequent urination, sterility; arthralgia due to wind-dampness, numbness and spasm of limbs, flaccidity of tendons and bones, gait difficulty; deficiency of kidney yang, dyspnea with coughing and shortness of breath. Icariin can increase cardio-cerebrovascular blood flow, promote hematopoietic function, immunological function and bone metabolism, and have efficacies such as tonifying the kidney to strengthen yang, anti-aging, anti-tumor, etc. Icaritin (IT) is a poly-hydroxy flavonoid monomer component in the plant, epimedium, in the genus *Epimedium* of the family Berberidaceae. Pharmacological studies have shown that IT has a stronger anti-osteoporosis effect than other flavonoid glycoside compounds in *epimedium*, and has an effect of promoting the activity of osteoblasts and inhibiting the activity of osteoclasts.

In recent years, icariin and icaritin, as important active components in *epimedium*, have drawn more and more interests from medical practitioners. For example, Chinese patent application CN101637467A discloses use of icaritin in preparing a medicament for the treatment of osteoporosis. U.S. Pat. No. 6399579 discloses use of icaritin in the treatment of sexual dysfunction. In "30 Cases of Combined Treatment of Traditional Chinese Medicine and Western Medicine of Chronic Idiopathic Thrombocytopenic Purpura" (published in "Jilin Journal of Traditional Chinese Medicine", 2010, Issue No. 7), Ningxia Qiang achieved relatively good therapeutic effects in the treatment of chronic idiopathic thrombocytopenic purpura by taking traditional Chinese medicine for invigorating the spleen and tonifying the kidney (Ginseng, Radix Astragali, Chinese Angelica, Fructus Corni, *Epimedium*, Fructus Psoraleae, etc.) on the basis of western medicine treatment. However, the medicine contains various active ingredients, and has complex mechanism of action. Therefore, it is necessary to conduct more detained studies on the mechanism and the efficacy. In "Studies on Effect of Icariin in Synergistically Inducing IL-2, 3 and 6" (published in "Chinese Journal of Immunology", 1996, Issue No. 1), Yong Zhao, etc. tested the effect of icariin in synergistically inducing IL-2, IL-3 and IL-6, respectively, by using dependent cell strain method, and the results showed that icariin, with PHA, can synergistically induce mononuclear cell of tonsil to produce IL-2, 3 and 6 in a dose-dependent manner, which suggested that icariin is an effective biological response modifier.

To date, there has been no report in the literature that icaritin has an activity in preventing or treating hematocytopenia, especially immune thrombocytopenia, or radiation- or chemical-induced bone marrow suppression.

SUMMARY OF THE INVENTION

An object of the present application is to provide a medicament for preventing and/or treating hematocytopenia, such as thrombocytopenia, especially immune thrombocytopenia, or a medicament for preventing and/or treating radiation- or chemical-induced bone marrow suppression. The present inventors have long been studying the pharmacological activities of icaritin, and recently discovered unexpectedly in a further research that icaritin shows unexpected activities in alleviating hematocytopenia as well as in treating thrombocytopenia.

In a first aspect, the present application relates to use of icaritin in the preparation of a medicament for preventing or treating hematocytopenia, in which the hematocytes or blood cells include white blood cells, red blood cells, neutrophils or platelets, and the hematocytopenia is mainly manifested by the reduction of white blood cells or platelets in the peripheral blood. The hematocytopenia includes radiation- or chemical-induced bone marrow suppression, or primary myelodysplasia.

In some specific embodiments, the present application provides use of icaritin in preventing or treating radiation- or chemical-induced bone marrow suppression. The chemical may be a chemotherapeutic agent which can induce bone marrow suppression, in particular a chemotherapeutic drug which can be used to treat cancers. Preferably, the chemotherapeutic drug used to treat cancer is Docetaxel; Tegafur, Gimeracil and Oteracil Potassium Capsules (S-1) or a combination thereof, but is not limited thereto. In Example 22 of the present application, which involves an experiment showing the effect of icaritin on the chemotherapy-induced bone marrow suppression in tumor-bearing mice, it has been shown that the combination of an antitumor drug (e.g. Docetaxel or Tegafur, Gimeracil and Oteracil Potassium Capsules) with icaritin leads to very significant increase in the total number of white blood cells, the number of platelets and the number of neutrophils in tumor-bearing mice in comparison with the group administered with the antitumor drug alone, while the body weight, food intake and living status of the animals in the groups administered with the combination showed no significant difference in comparison with the blank control group. In other words, icaritin in combination can not only significantly increase blood cells in tumor-bearing mice, but also have very low toxic side effects. In Example 23 of the present application, which involves an experiment showing the effect of icaritin on the number of blood cells in mice receiving $^{60}$Co radiation, it has been shown that the combination of icaritin with $^{60}$Co radiation can effectively increase the numbers of white blood cells and platelets in the mice, and its effect of increasing blood cells is significantly superior to that in the group administered with epimedium extract. The above Examples have demonstrated that icaritin has unexpected effects of alleviating bone marrow suppression induced by radiotherapy or chemicals.

In addition, in Example 24 of the present application, which involves an experiment showing the effect of icaritin on white blood cells and platelets in NOD/Ltj mice in Example 24 of the present application, it has been demonstrated that the high-dose and low-dose icaritin groups show significant increase in the numbers of white blood cells and platelets in NOD/Ltj mice, and their effects of increase are significantly superior to interleukin, a commonly used therapeutic drug. This suggests that icaritin also has good therapeutic effect on primary myelodysplasia since NOD/Ltj mice are those with an abnormal immune system in which the numbers of platelets and white blood cells are obviously lower than those in normal mice.

In some embodiments of the present application, the present application provides use of icaritin in the preparation of a medicament for preventing or treating thrombocytopenia. The thrombocytopenia may be immune thrombocytopenia, in particular chronic idiopathic thrombocytopenic purpura. The thrombocytopenia may also be secondary thrombocytopenia induced by bone marrow suppression. In Example 26 of the present application, it has been demonstrated that icaritin shows a positive therapeutic effect in chronic ITP model rats, in which the high-dose group and the medium-dose group show a very significant effect of increasing platelets in the rats (P<0.01), and their effect of increasing platelets is superior to that of the positive control, icariin. Accordingly, the pharmaceutical composition of the present application may be used in the preparation of a pharmaceutical formulation for treating thrombocytopenia, especially for treating immune thrombocytopenia.

In the above medical uses of the present application, the thrombocytopenia is preferably secondary thrombocytopenia induced by bone marrow suppression, in which the bone marrow suppression is that induced by chemical drugs. In Example 28 of the present application, it has been demonstrated that the icaritin groups and the icariin group showed a positive therapeutic effect on thrombocytopenia induced by cyclophosphamide in mice, and can increase the number of platelets in the model of thrombocytopenia induced by cyclophosphamide in mice, wherein each of the icaritin groups is superior to the icariin group in increasing the number of platelets in the model of thrombocytopenia induced by cyclophosphamide in mice, icaritin shows dose dependence in increasing the number of platelets in the model of thrombocytopenia induced by cyclophosphamide in mice, and the high-dose icaritin group and the medium-dose icaritin group show significant difference in comparison with the icariin group.

In a further aspect, the present application provides a method for preventing or treating hematocytopenia or thrombocytopenia using icaritin. The method comprises administering an effective amount of icaritin to an individual in need thereof. The individual is preferably a human.

In the use of icaritin in the preparation of a medicament for treating hematocytopenia or thrombocytopenia as disclosed in the present application, icaritin is typically administered in the form of a pharmaceutical composition, and may be administered orally or non-orally, or safely administered orally or non-orally as a composition formed with pharmaceutically acceptable carriers, excipients and other additives (such as tablets, sustained release formulations, capsules, injections, and solutions). The dosage for oral administration to human may be 0.1 mg/kg/d to 100 mg/kg/d. Non-oral administration includes, but is not limited to, subcutaneous, intradermal, intra-arterial, intravenous, intramuscular, arthrous, intrathecal, intracranial, intrathoracic, intraperitoneal injection or infusion, and transnasal, buccal, sublingual, tracheal, urethral, rectal or focal topical administration, and so on. Administration by injection is preferred, wherein the dosage of icaritin administered to human is preferably 0.01 mg/kg to 10 mg/kg.

In addition, according to the present application, icaritin may be used as the sole active ingredient for preventing and/or treating the diseases associated with hematocytopenia or thrombocytopenia, preferably for preventing and/or treating radiation- or chemical-induced bone marrow suppression, or immune thrombocytopenia; or used in combination with other drug(s) for such prevention and/or treatment. Said other drug(s) which may be administered in combination with or prepared into a pharmaceutical composition with icaritin may be one or more other drugs for treating leukocytopenia (for example vitamin B4, leucogen, batyl alcohol, coenzyme A), or one or more other drugs which can increase the amount of platelets (for example interleukin-II, low-dose glucocorticoids such as prednisone, etc.) for preventing or treating hematocytopenia, particularly for preventing or treating bone marrow suppression. When these drugs are administered in combination with or prepared into a pharmaceutical composition with icaritin for treating bone marrow suppression, the effect of icaritin in increasing the amount of platelets or white blood cells can be further enhanced.

According to some embodiments, when icaritin of the present application is used in combination with other drug, the weight ratio of the two drugs may be appropriately adjusted according to the condition and symptoms of the patient, and weight ratio of the other drug to icaritin is preferably in the range of (0.005-100):1, more preferably (0.005-50):1, still more preferably (0.01-100):1, for example (0.05-25):1.

The routes of administration of icaritin and optionally other drug include parenteral routes and non-parenteral routes, wherein the non-parenteral routes include, but are not limited to, subcutaneous, intradermal, intra-arterial, intravenous, intramuscular, arthrous, intrathecal, intracranial, intrathoracic, and intraperitoneal injection or infusion, and transnasal, buccal, sublingual, tracheal, urethral, rectal or focal topical administration. When icaritin is used for preventing and/or treating radiation- or chemical-induced bone marrow suppression, icaritin may be administered before, after, or during the radiotherapy or chemotherapy. When icaritin is administered in combination with other drug, icaritin and the other drug may be administered simultaneously or in sequence.

Another aspect of the present application relates to a pharmaceutical composition (or formulation) for preventing or treating the diseases associated with hematocytopenia or thrombocytopenia, which comprises icaritin and pharmaceutically acceptable excipients. The pharmaceutical composition is preferably used for preventing or treating radiation- or chemical-induced bone marrow suppression.

Those skilled in the art may select proper pharmaceutical excipients depending on actual requirements, and prepare the formulation of the present application by methods known in the art. The formulation includes, but is not limited to, solid, liquid, oil, emulsion, gel, aerosol, inhalant, spray, capsule, pill, patch, and suppository. When administered orally, the composition can be formulated into tablets, granules or capsules. In order to prepare an oral pharmaceutical composition, lactose or starch may be used as a carrier. Gelatin, carboxymethyl cellulose sodium, methyl cellulose, polyvinylpyrrolidone, etc. are suitable binders or granulating agents. As a disintegrating agent, starch or microcrystalline cellulose may be selected. Talc powder, colloidal silica, glyceryl stearate, calcium or magnesium stearate, and the like are often used as suitable anti-sticking agents and lubricants. Tablets may be prepared by compressing wet granules, for example. The active ingredient is mixed with the carrier and optionally with a portion of the disintegrating agent to give a mixture, which is granulated in a suitable device with an aqueous, alcoholic or aqueous-alcohol solution of the binders. The granules are dried and then added with the remaining disintegrating agent, the lubricants and the anti-sticking agents, and the resulted mixture is tableted. The administration may be carried out in the form of an injection, while the dosage may vary according to the subject being treated, the route of administration, the symptoms, and other factors. The actual dosage of the icaritin administered should be determined by a doctor according to relevant conditions including the state of the subject being treated, the selected route of administration, age, body weight, and individual response of the patient to the drug, severity of the patient's symptoms, and the like. The injection formulation is one of injectable solution, freeze-dried powder for injection, and infusion formulation. In the injection formulation, the pharmaceutical excipient is one or more of mannitol, glucose, sorbitol, PEG, ethanol and normal saline. The injection formulation comprising PEG is preferred.

In the icaritin-containing pharmaceutical formulation suitable for the above medical use, each formulation unit may contain icaritin in an amount of 0.1 to 500 mg.

Definition of Terms

As used herein, the "icaritin" may be obtained by extraction, biological synthesis, or chemical synthesis, and may include icaritin, a pharmaceutically acceptable salt or hydrate thereof. The icaritin of the present application contains icaritin with purity (such as that determined by HPLC) of ≥90%, ≥95%, or ≥98%. All the methods for preparing icaritin disclosed in the prior art before the filing date of the present application may be used as processes for preparing the icaritin of the present application.

In the present application, the term "bone marrow suppression" refers to a condition wherein the components of blood cells, including white blood cells, red blood cells, neutrophils and platelets, are reduced individually or simultaneously, which is manifested by the reduction in the production of blood cells. Healthy bone marrow produces a large amount of red blood cells, white blood cells and platelets every day. Under bone marrow suppression, these cells produced by bone marrow are reduced. One characteristic of bone marrow suppression is the reduction in the production of white blood cells. This reduction in the production of white blood cells may be caused by a certain treatment, especially treatment of cancers, such as chemotherapy and radiotherapy. Preferably, the bone marrow suppression of the present application is manifested by the reduction in the number of white blood cells or platelets in the peripheral blood, or myelodysplasia. In some embodiments, the reduction in the number of white blood cells in the peripheral blood refers to the reduction in the number of neutrophils in the peripheral blood.

The "radiation" may be that received during a radiation therapy, or that received due to other factors such as work, environment, etc. Preferably, the radiation in the above-described uses is that received during a radiation therapy, such as a radiation therapy for treating cancers.

The term "chemical" may refer to any drug or chemical agent which can cause reduction in the production of blood cells. In one embodiment, the chemical in the above-described uses is a chemotherapeutic agent used for treating cancers. The chemotherapeutic agent includes alkylating agent drugs, antimetabolic drugs, antibiotic drugs, plant drugs, hormone drugs, and so on, but is not limited thereto. Among them, the alkylating agent drugs include, but are not limited to, nitrogen mustards, cyclophosphamide, thiotepa, lomustine, myleran, dacarbazine, and procarbazine; the antimetabolic drugs include, but are not limited to, fluorouracil (5-FU), ftorafur (FT-207), tegadifur (difuradin FD-1), tegafur-uracil (UFT), furtulon (5-DFUR), methotrexate (MTX), aminopterin (BaiXueNing), cytosine arabinoside (Ara-c), cyclocytidine, chlorine cyclocytidine, hydroxyurea (HU), inosine dialdehyde, adenosine dialdehyde (adenosinedi-ialde-hgde), guanazole, and 6-mercaptopurine (6-MP); the antibiotic drugs include, but are not limited to, penicillin antibiotics, cephalosporin antibiotics, aminoglycoside antibiotics, macrolide antibiotics, sulfonamide antibiotics, quinolone antibiotics, and furan antibiotics; the plant drugs are plant-derived drugs, including the traditional Chinese medicines and the active fractions or individual ingredients obtained from a plant through the modern extraction and separation means; the hormone drugs include, but are not limited to, corticosteroids, adrenal cortex hormones, noradrenalines, progestogens, estrogens, androgens; and so on.

In the present application, the term "pharmaceutically acceptable excipients" refers to any substance which does not interfere with the physiological effects of icaritin and is not toxic to a subject including human. Suitable pharmaceutical excipients have been described in detail in Encyclopedia of Pharmaceutical Excipients (page 123, Sichuan Publishing House of Science and Technology, published in 1993, LUO Mingsheng and GAO Tianhui, Eds.). For example, the pharmaceutical excipients commonly used for preparing microemulsion formulations include, but are not limited to, soybean oil, polyoxyethylene-23-lauryl ether, 1,2-propanediol, hydrogenated coco-glyceride, lauroyl polyethylene glycol-32-glyceride, polyethylene glycol 3350, safflower oil, cotton seed oil, and decaglycerol monostearate; the pharmaceutical excipients commonly used for preparing dripping pill formulations include, but are not limited to, polyethylene glycol 6000, and polyethylene glycol 1000; the pharmaceutical excipients commonly used for preparing capsule formulations include, but are not limited to, lactose and corn starch. The pharmaceutical carriers commonly used for preparing soft capsule formulations include, but are not limited to, medium-chain fatty acid glycerides, polyoxyethylene castor oil, 1,2-propanediol, etc.

In the present application, the term "thrombocytopenia" refers to a disease in which the reduction in platelets in the peripheral blood causes bleeding of skin mucosa and internal organs, which is mainly manifested by spontaneous skin petechiae and ecchymosis, mucosal bleeding, epistaxis and gum bleeding, occurrence of purple blisters in oral mucosa and tongue, etc. It is a clinically common disease characterized by coagulation disorders and bleeding or more severely hemorrhoea and life-threatening, and represents about 30% of clinical hemorrhagic diseases. It may be immune thrombocytopenia or secondary thrombocytopenia.

The "immune thrombocytopenia" is a hemorrhagic disease caused by disorders of the immune system, and mainly refers to immune thrombocytopenic purpura (ITP). ITP is a relatively common hemorrhagic disease, and may occur at any age stage with an estimated ITP incidence rate of population being 1/10000. The clinical manifestations thereof include skin petechiae and ecchymosis, bleeding in skin mucous, while critically ill patients may suffer from joint pain or abdominal pain, hemafecia, hematemesis, collapse or the like. More severely, it may develop into purpura nephritis.

The "primary thrombocytopenic purpura" or "idiopathic thrombocytopenic purpura" is one of immune thrombocytopenia. It is an acquired hemorrhagic disease with unknown cause, and is characterized mainly by reduced platelets, normal or increased megakaryocytes in bone marrow normal, and lack of any cause. This disease usually occurs in children and young adults. It is usually acute in children, and chronic in adults. It is characterized by the presence of anti-platelet antibodies in the blood circulation, which destructs the platelets excessively to cause purpura; and by normal or increased megakaryocytes in bone marrow normal, and immaturation.

The "secondary thrombocytopenia", also referred to as acquired thrombocytopenia, is thrombocytopenia secondary to other diseases or induced by drug treatment of diseases, which involves a great number of diseases and drugs. It includes drug-related immune thrombocytopenia, other immune thrombocytopenia such as Evans syndrome, chronic lymphocytic leukemia, various acute leukemia, lymphoma, systemic lupus erythematosus, rheumatoid arthritis, hyperthyreosis, etc. The secondary thrombocytopenia described in the present application is mainly induced by bone marrow suppression due to radiation or chemical drugs.

The icaritin of the present application, in preventing or treating diseases associated with hematocytopenia, especially in preventing or treating bone marrow suppression induced by radiation or chemicals, shows at the least the following advantages (but not limited thereto):

1) It prevents the reduction of white blood cells while treating cancer, and even increases the number of neutrophils, thereby improving the efficacy of chemotherapy on tumors, prolonging the surviving time and improving surviving quality of cancer patients. Through an experiment showing the effect of icaritin on bone marrow suppression induced by chemotherapy in tumor-bearing mice, it has been found that icaritin has an unexpected effect of alleviating bone marrow suppression. Specifically, in comparison with the model group, both the total number of white blood cells and the number of neutrophils in the icaritin groups both increase with very significant difference ($P<0.01$) or with significant difference ($P<0.05$). Meanwhile, in comparison with the docetaxel group and the Tegafur, Gimeracil and Oteracil Potassium Capsules group, both the total number of white blood cells and the number of neutrophils in the icaritin groups increase dramatically with very significant difference ($P<0.01$).

2) It can be administered at the same time of the chemotherapy with other drugs, and can also be administered prophylactically, is not administered only when leukocytopenia occurs, and thus reduces the side effects to some extent. It can also been seen from the test results that icaritin, as an anti-cancer agent, even when administered in combination with docetaxel or Tegafur, Gimeracil and Oteracil Potassium Capsules, functions to inhibit tumor growth and at the same time alleviates bone marrow suppression induced by docetaxel or Tegafur, Gimeracil and Oteracil Potassium Capsules. Accordingly, icaritin can be administered at the same time of the chemotherapy with other drugs, and can also be administered prophylactically, and is not administered only when leukocytopenia occurs. This promotes bone marrow hematopoiesis and increases the numbers of white blood cells and neutrophils while ensuring the tumor-inhibiting rate, and reduces the side effects to some extent. As can be seen from the test results in Table 1, in comparison with the model group, the mice in the groups of icaritin alone or in combination show no significant difference in the body weights during the administration, and the animals also show no significant difference in the food intake and living status. This demonstrates that icaritin has no significant toxic side effects as an antitumor agent and a drug for alleviating bone marrow suppression.

3) It also has a significant effect in preventing or treating bone marrow suppression occurred during radiotherapy. It has been found through an experiment showing the effect of icaritin on white blood cells and platelets in tumor-bearing mice receiving 4 Gy of $^{60}$Co radiation (Table 3) that icaritin has an unexpected effect of alleviating bone marrow suppression induced by radiotherapy. Specifically, both the total number of white blood cells and the total number of platelets in the icaritin group increase with very significant difference (P<0.01) or with significant difference (P<0.05) in comparison with the model group; and with significant difference (P<0.05) in comparison with the epimedium extract group.

Icaritin shows significant therapeutic effects on thrombocytopenia induced by various factors. In Example 26 of the present application, it has been demonstrated that icaritin is superior to the positive control, icariin, in increasing platelets in the chronic ITP model rats. The high-dose group and the medium-dose group show very significant effects of increasing platelets in rats (P<0.01). In Example 27 of the present application, it has been demonstrated that icaritin also has a positive therapeutic effect of treating active immune thrombocytopenia in mice.

Icaritin also shows a positive therapeutic effect on secondary thrombocytopenia induced by bone marrow suppression, which suggests that it can be administered in combination with other chemical drugs to reduce the damage caused by chemicals (such as chemotherapeutic drugs) to the body. In Example 28 of the present application, it has been demonstrated that the icaritin groups and the icariin group show a positive therapeutic effect on thrombocytopenia induced by cyclophosphamide in mice, and can increase the number of platelets in the model of thrombocytopenia induced by cyclophosphamide in mice, wherein each of the icaritin groups is superior to the icariin group in increasing the number of platelets in the model of thrombocytopenia induced by cyclophosphamide in mice, and the high-dose icaritin group and the medium-dose icaritin group show significant difference in comparison with the icariin group.

Icaritin is an effective and active ingredient extracted from the traditional Chinese medicine, epimedium. It shows explicit efficacy in treating thrombocytopenia and is suitable for drug combination. In addition, it has very low toxic side effects, which can greatly increase the compliance of patients, thereby ensuring the therapeutic effects of the drug. Furthermore, there are currently many methods for preparing icaritin, which are simple and inexpensive. Therefore, the cost for treating thrombocytopenia patients can be greatly reduced.

Specific Embodiments

The present application will be further described with the following embodiments. However, the present application is not limited to the following Examples.

EXAMPLE 1

Icaritin Microemulsion Formulation

| Icaritin | 10 g |
|---|---|
| Soybean oil | 35 g |
| Polyoxyethylene-23-lauryl ether | 60 g |
| 1,2-Propanediol | 30 g |

Preparation process: The prescribed amounts of soybean oil, polyoxyethylene-23-lauryl ether, and 1,2-propanediol were weighed, mixed and stirred well, followed by adding and dissolving icaritin, during which sonication may be used to accelerate the dissolution, to give a clear solution, which was the icaritin microemulsion formulation. The particle size thereof was determined by a laser particle size analyzer, and the average particle size was 15 nm.

EXAMPLE 2

Icaritin Microemulsion Formulation

| Icaritin | 0.1 g |
|---|---|
| Hydrogenated coco-glyceride | 5 g |
| Lauroyl polyethylene glycol-32-glyceride | 20 g |
| 1,2-propanediol | 5 g |
| Polyethylene glycol 3350 | 20 g |

Preparation process: The prescribed amounts of hydrogenated coco-glycerides, lauroyl polyethylene glycol-32-glyceride, 1,2-propanediol, and polyethylene glycol 3350 were weighed, mixed and stirred well, followed by adding and dissolving icaritin, during which sonication may be used to accelerate the dissolution, to give a clear solution, which was the icaritin microemulsion formulation. The particle size was determined by a laser particle size analyzer, and the average particle size was 40 nm.

EXAMPLE 3

Icaritin Injection

| Icaritin | 500 g |
|---|---|
| PEG-400 | 2 L |
| Ethanol | 0.5 L |
| 0.9% NaCl Solution | Added up to 10 L |

Preparation process: Icaritin was added to the prescribed amount of PEG-400, and stirred to dissolve, followed by adding 0.9% NaCl solution to 10 L. The mixture was stirred well, followed by adding 0.5% activated carbon for injection, stirring, and removing the carbon, to give the icaritin injection.

EXAMPLE 4

Icaritin Injection

| Icaritin | 10 g |
|---|---|
| Ethanol | 2 L |
| Tween-80 | 1500 g |
| Water for injection | Added up to 10 L |

Preparation process: The prescribed amounts of ethanol and tween-80 were mixed well, followed by adding, stirring and dissolving icaritin, and adding water for injection up to 10 L. The mixture was stirred well, followed by adding 0.5% activated carbon for injection, stirring, and removing the carbon, to give the icaritin injection.

EXAMPLE 5

Icaritin Injection

| Icaritin | 1 g |
|---|---|
| Ethanol | 3.3 L |
| Water for injection | Added up to 10 L |

Preparation process: Icaritin was added to the prescribed amount of ethanol, stirred to dissolve, followed by adding water for injection up to 10 L. The mixture was stirred well, followed by adding 0.5% activated carbon for injection, stirring, and removing the carbon, to give the icaritin injection.

EXAMPLE 6: Icaritin Dripping Pill Formulation

| | |
|---|---|
| Icaritin | 5.0 g |
| Polyethylene glycol-6000 | 14.5 g |
| Polyethylene glycol-1000 | 5.0 g |
| | Made into 1000 pills |

Preparation process: The prescribed amount of icaritin which had pass through a 100-mesh sieve was weighed and added to a mixed liquid of the prescribed amounts of polyethylene glycol 6000 and polyethylene glycol 1000 which had been heated and melted in a water bath. The mixture was stirred well, filled into a dropping bottle, dripped at 95±2° C. into a glass condensing column containing 4-6 mL of methyl silicone oil, and taken out after formation. The icaritin dripping pill formulation was obtained after the adsorbed methyl silicone oil was drawn off with absorbent paper.

EXAMPLE 7

Icaritin Enteric Soft Capsule Formulation

| | |
|---|---|
| Formula of the contents: | |
| Icaritin | 10 g |
| Absolute ethanol | 10 g |
| 1,2-Propanediol | 10 g |
| Polyoxyethylene castor oil | 50 g |
| Medium-chain fatty acid glyceride | 20 g |
| Formula of the capsule shell: | |
| Gelatin | 10 g |
| Glycerol | 5 g |
| Formula of the enteric coating solution: | |
| Eudragit L30D-55 | 100 g |
| Triethyl citrate | 3 g |
| Talc powder | 7.5 g |
| Purified water | 200 g |

Preparation process: The prescribed amounts of medium-chain fatty acid glyceride, polyoxyethylene castor oil, 1,2-propanediol, and absolute ethanol were weighed, mixed, and stirred well, followed by adding and dissolving icaritin, during which sonication may be used to accelerate the dissolution, to give a clear concentrate, which was the icaritin microemulsion concentrate. The microemulsion concentrate obtained as above was diluted with water in a weight ratio of 1:10-20 to give a clear solution, which was the microemulsion content for the soft capsule. The prescribed amounts of gelatin, glycerol, and purified water were mixed well and compressed into the capsule shell. Further, the prescribed amounts of Eudragit L30D-55, triethyl citrate, talc powder, and purified water were mixed well to give the enteric coating solution. The microemulsion contents for the soft capsule containing icaritin were wrapped with the capsule shell to give the soft capsule, which was then coated with the enteric coating to give the enteric soft capsule.

EXAMPLE 8

Icaritin Capsule Formulation

| | |
|---|---|
| Icaritin | 100 g |
| Corn starch | 130 g |
| Magnesium stearate | 5 g |

Preparation process: 100 g of icaritin, 120 g of lactose and 130 g of corn starch were mixed in a mixer for 10-15 minutes, followed by adding 5 g of magnesium stearate and mixing for 1-3 minutes, and then filled into 1000 capsule shells, to give the icaritin capsule formulation.

EXAMPLE 9

Icaritin Tablets

| | |
|---|---|
| Icaritin | 5000 g |
| Microcrystalline cellulose | 200 g |
| Carboxymethyl starch sodium | 8 g |
| Magnesium stearate | 1.5 g |
| 8% Starch slurry | Appropriate amount |

Preparation process: Icaritin and the excipients microcrystalline cellulose and carboxymethyl starch sodium were mixed well, followed by adding an appropriate amount of starch slurry to produce a soft material, which was passed through a 16-mesh sieve and granulated. The wet granulate was dried at 60° C., and the dried granulate was passed through a 20-mesh sieve and granulated. Fine powders in the dry granulate were sieved out and mixed well with magnesium stearate, then mixed well with the dry granulate, and compressed into tablets with about 200 mg per tablet.

EXAMPLE 10

Icaritin Powder for Injection

| | |
|---|---|
| Icaritin | 100 g |
| Glucose | 20 g |
| Water for injection | Added up to 1000 ml |
| Freeze-dried | Totally 6000 vials |

Preparation process: The prescribed amount of icaritin raw material for injection was weighed and added into an appropriate amount of water for injection to dissolve. Then, a specified amount of which had been subjected to sterilization and depyrogenation treatments in advance was added and mixed well, followed by adding water for injection up to the prescribed volume, i.e. 1000 ml. To the above solution was added 5 g of activated carbon for injection, heated at 60-80° C. for 30 minutes, filtered with a filter membrane, and the filtrate was collected. The above filtrate was subjected to positive-pressure aseptic filtration with a sterilizing filter according to aseptic manipulation, and then filtered with a 0.22 μM microporous filter membrane. The filtrate was subjected to pyrogen test and test of contents of the semi-finished product before being sub-packaged in penicillin vials. The material was pre-frozen at −40° C. in a special freeze-drying box for 1.5-3.5 hours, sublimed under vacuum, and warmed and dried after 90% of the free water was removed (the highest temperature not exceeding 35° C.). After freeze-drying, the icaritin powder for injection was obtained.

EXAMPLE 11

Icaritin Injection

| | |
|---|---|
| Icaritin | 10 mg |
| Propanediol | 3 ml |
| Ethanol | 0.5 ml |
| 0.9% NaCl solution | Added up to 10 ml |

Preparation process:

The prescribed amounts of propanediol and ethanol were mixed well, followed by adding icaritin, and stirring to dissolve. The prescribed amount of 0.9% NaCl solution was added and mixed well, followed by adding 0.5% activated carbon for injection, stirring and removing the carbon, to give the icaritin injection.

EXAMPLE 12

Icaritin Injection

| | |
|---|---|
| Icaritin | 10 mg |
| PEG-400 | 2 ml |
| 0.9% NaCl solution | Added up to 10 ml |

Preparation process: The prescribed amount of PEG-400 was added to icaritin, and stirred to dissolve, followed by adding 0.9% NaCl solution up to 10 ml. The mixture was stirred well, followed by adding 0.5% activated carbon for injection, stirring and removing the carbon, to give the icaritin injection.

EXAMPLE 13

Icaritin Injection

| | |
|---|---|
| Icaritin | 50 mg |
| Ethanol | 3.5 ml |
| Tween-80 | 1.5 g |
| Water for injection | Added up to 10 ml |

Preparation process: The prescribed amounts of ethanol and tween-80 were mixed well. Icaritin was added and stirred to dissolve. 0.9% NaCl solution was added up to 10 ml and stirred well, followed by adding 0.5% activated carbon for injection, stirring and removing the carbon, to give the icaritin injection.

EXAMPLE 14

Icaritin Injection

| | |
|---|---|
| Icaritin | 30 mg |
| Ethanol | 2 ml |
| Tween-80 | 1.5 g |
| Water for injection | Added up to 10 ml |

Preparation process: The prescribed amounts of ethanol and tween-80 were mixed well. Icaritin was added and stirred to dissolve. 0.9% NaCl solution was added up to 10 ml and stirred well, followed by adding 0.5% activated carbon for injection, stirring and removing the carbon, to give the icaritin injection.

EXAMPLE 15

Icaritin Injection

| | |
|---|---|
| Icaritin | 5 mg |
| Ethanol | 2 ml |
| Tween-80 | 1.5 g |
| Water for injection | Added up to 10 ml |

Preparation process: The prescribed amounts of ethanol and tween-80 were mixed well. Icaritin was added and stirred to dissolve. 0.9% NaCl solution was added up to 10 ml and stirred well, followed by adding 0.5% activated carbon for injection, stirring and removing the carbon, to give the icaritin injection.

EXAMPLE 16

Icaritin Injection

| | |
|---|---|
| Icaritin | 20 mg |
| Ethanol | 3.3 ml |
| Water for injection | Added up to 10 ml |

Preparation process: Icaritin was added to the prescribed amount of ethanol and stirred to dissolve. Water for injection was added up to 10 ml and stirred well, followed by adding 0.5% activated carbon for injection, stirring and removing the carbon, to give the icaritin injection.

EXAMPLE 17

Icaritin Injection

| | |
|---|---|
| Icaritin | 10 mg |
| Ethanol | 3.3 ml |
| Water for injection | Added up to 10 ml |

Preparation process: Icaritin was added to the prescribed amount of ethanol and stirred to dissolve. Water for injection was added up to 10 ml and stirred well, followed by adding 0.5% activated carbon for injection, stirring and removing the carbon, to give the icaritin injection.

EXAMPLE 18

Icaritin Tablets

| | |
|---|---|
| Icaritin | 15 g |
| Starch | 140 g |
| Dextrin | 120 g |
| 50% Ethanol | Appropriate amount |
| Magnesium stearate | 1.0 g |

Preparation process: The prescribed amounts of icaritin, starch and dextrin were mixed well. An appropriate amount of 50% ethanol was then added to the mixed powder, and mixed well to prepare a soft material, which was passed through an 18-mesh nylon sieve to produce a wet granulate. The wet granulate was dried at around 60° C., while controlling the water content in the dry granulate at below 1.5%. The dry granulate was passed through a 20-mesh sieve to granulate, and then mixed with magnesium stearate and compressed into tablets.

EXAMPLE 19

Icaritin Capsules

| | |
|---|---|
| Icaritin | 10 g |
| Microcrystalline cellulose | 300 g |
| Micronized silica gel | 12 g |

Preparation process: Icaritin, microcrystalline cellulose and micronized silica gel were ground, passed through a 100-mesh sieve, mixed well, and directly filling into capsules.

EXAMPLE 20

Icaritin Granules

| | |
|---|---|
| Icaritin | 45 g |
| Starch | 200 g |
| Dextrin | 50 g |
| Sucrose powder | 50 g |
| 80% Ethanol | Appropriate amount |

Preparation process: The prescribed amounts of icaritin, starch, dextrin and sucrose powder were weighed and mixed well. An appropriate amount of 80% ethanol was then added to the mixed powder and mixed well to give a soft material, which was passed through an 18-mesh nylon sieve to produce a wet granulate. The wet granulate was dried at around 60° C., and then passed through a 20-mesh sieve and granulated, and then subpackaged to give the granules of icaritin.

EXAMPLE 21

Sustained Release Tablets of Icaritin

| | |
|---|---|
| Icaritin | 10 g |
| Hydroxypropyl methyl cellulose | 80 g |
| Polyvinylpyrrolidone | 100 g |
| Lactose | 85 g |
| Micronized silica gel | 100 g |

Preparation process: The prescribed amounts of icaritin, lactose and the sustained release agent hydroxypropyl methyl cellulose were mixed well, followed by adding the binder polyvinylpyrrolidone. The mixture was granulated and dried at 40-80° C., and the dry granulate was granulated. The prescribed amount of the lubricant micronized silica gel was added to the dry granulate and mixed well, and the mixture was subjected to profiled pressing into tablets.

EXAMPLE 22

Effect of Icaritin on Chemotherapy-Induced Bone Marrow Suppression in Tumor-Bearing Mice 1. Materials 1.1 Test animals: Kunming mice (purchased from Chinese National Institute for the Control of Pharmaceutical and Biological Products, License of Laboratory Animal No.: SCXK II-00-0010), half male and half female, 7 weeks old, 18-22 g, test temperature (20±1) ° C., humidity 40%~70%, free access to water, normal feeding.

1.2 Test reagents:

| Test reagents | Manufacturers or sources |
|---|---|
| Icaritin Microemulsion Formulation | Prepared according to the process of Example 1, purity of icaritin: 99.3% |
| Docetaxel | Purchased from Hangzhou Sanofi-Aventis Minsheng Pharmaceuticals Co. Ltd. |
| Tegafur, Gimeracil and Oteracil Potassium Capsules | Purchased from Shandong Xinshidai Medicine Industry Co., Ltd. |
| Mice ascites tumor s180 cells | Purchased from Shanghai Aiyan Biological Technology Co. Ltd. |
| 1640 Culture medium | Purchased from Shanghai Yansheng Biochemical Agents Co. Ltd. |

2. Method:

Mice ascites tumor s180 cells were conventionally incubated in 1640 culture medium, at 37° C., 5% $CO_2$, and passaged once every two days in average. The cells in the logarithmic growth phase were prepared into a single-cell suspension having a density of $3.0 \times 10^7$ cells/ml with normal saline, which was injected into the abdominal cavities of mice under sterile conditions. Seven days after inoculation, significant swelling of the abdominal cavities of mice can be seen. As this time, the mice were executed by cervical vertebra luxation, put into a beaker containing 75% ethanol and soaked for 2-3 minutes. The sterilized mice were placed into an ultraclean bench, and the abdomens were exposed. The ascites was drawn with a sterile syringe and put into a sterile reagent bottle for further use. The above ascites was counted with trypan blue, diluted with normal saline to adjust to $2.0 \times 10^7$ cells/ml, and inoculated at the right armpit of the mice with 0.2 ml for each mouse.

The inoculated mice were randomly divided into 6 groups, with 10 animals in each group and half male and half female.

Group 1, the model control group: the test animals were intraperitoneally injected with 0.9% normal saline (same for the following experiments);

Group 2, the docetaxel group: 75 mg/m²/d of docetaxel;

Group 3, the Tegafur, Gimeracil and Oteracil Potassium Capsules group: 222.2 mg/m²/d of Tegafur, Gimeracil and Oteracil Potassium Capsules;

Group 4, the icaritin group: 10 mg/kg/d of the icaritin microemulsion formulation;

Group 5, the D+I group (docetaxel+icaritin group): 75 mg/m²/d of docetaxel+10 mg/kg/d mg/kg/d of icaritin;

Group 6, the T +I group (Tegafur, Gimeracil and Oteracil Potassium Capsules+icaritin group): 222.2 mg/m²/d of Tegafur, Gimeracil and Oteracil Potassium Capsules+10 mg/kg/d of icaritin.

Docetaxel and icaritin were administered by tail intravenous injection with an administration volume of 10 ml/kg for each. Tegafur, Gimeracil and Oteracil Potassium Capsules was intragastrically administered with an administration volume of 40 ml/kg. Each group was administered once a day for totally 10 days. During the test, the animals were observed every day for their food and water uptake, survival conditions and behaviors, and measured for their body weights every day. After the test was ended, the mice were anaesthetized and anatomized. Blood was collected from abdominal aorta for routine blood test, and the total number of white blood cells, the total number of platelets and the total number of neutrophils were determined.

3. Experimental results:

TABLE 1

Effect of icaritin on body weights of tumor-bearing mice

| Groups | Sample n. | Before Administration (g) | Day 5 after Administration (g) | Day 10 after Administration (g) |
|---|---|---|---|---|
| Model Control Group | 10 | 21.2 ± 2.6 | 30.3 ± 4.1 | 30.3 ± 4.3 |
| Docetaxel Group | 10 | 21.2 ± 1.8 | 28.1 ± 2.5 | 27.2 ± 3.2 |
| Tegafur, Gimeracil and Oteracil Potassium Capsules Group | 10 | 21.3 ± 2.3 | 29.6 ± 3.2 | 30.0 ± 3.6 |
| Icaritin Group | 10 | 21.1 ± 3.0 | 27.9 ± 4.2 | 27.9 ± 3.8 |
| D + I Group | 10 | 21.0 ± 2.9 | 28.4 ± 3.7 | 27.3 ± 3.5 |
| T + I Group | 10 | 21.3 ± 3.5 | 28.8 ± 3.0 | 30.1 ± 4.9 |

It can be seen from the test results in Table 1 that, in comparison with the model group, the mice in the groups of icaritin alone and in combination showed no significant difference in their body weights during the administration period. The animals also showed no significant differences in the food and water uptake and the survival conditions. This suggested that icaritin had no significant toxic side effect as an antitumor agent and a drug for alleviating bone marrow suppression.

($P<0.05$). Meanwhile, in comparison with the docetaxel group and the Tegafur, Gimeracil and Oteracil Potassium Capsules group, the total number of white blood cells, the number of platelets and the number of neutrophils of the mice in the icaritin group all increased dramatically with very significant difference ($P<0.01$).

It can also been seen from the test results that when icaritin, as an anti-cancer agent, was administered in combination with docetaxel or Tegafur, Gimeracil and Oteracil Potassium Capsules, it functioned to inhibit tumor growth and at the same time alleviated bone marrow suppression induced by docetaxel or Tegafur, Gimeracil and Oteracil Potassium Capsules. Accordingly, icaritin can be administered at the same time of the chemotherapy with other drugs, and can also be administered prophylactically, and can be not administered only when leukocytopenia occurred. It was able to promote bone marrow hematopoiesis and increase the numbers of white blood cells and neutrophils while ensuring the tumor-inhibiting rate, and reduces to some degree the side effects.

TABLE 2

Effect of icaritin on neutrophils in the white blood cells in tumor-bearing mice

| Groups | Sample n. | White blood cells ($10^9$/L) | Neutrophils ($10^9$/L) | Platelets ($10^9$/L) |
|---|---|---|---|---|
| Model Control Group | 10 | 2.831 ± 0.32 | 1.128 ± 0.18 | 508.3 ± 38.6 |
| Docetaxel Group | 10 | 2.773 ± 0.46 | 0.670 ± 0.12 | 450.6 ± 30.5 |
| Tegafur, Gimeracil and Oteracil Potassium Capsules Group | 10 | 2.703 ± 0.37 | 0.695 ± 0.09 | 432.9 ± 34.8 |
| Icaritin Group | 10 | 3.530 ± 0.31[##$$] | 1.316 ± 0.15[#$$] | 687.4 ± 37.2[##] |
| D + I Group | 10 | 3.288 ± 0.34[#*$$] | 1.301 ± 0.16[#$$] | 598.7 ± 25.8[#] |
| T + I Group | 10 | 2.895 ± 0.43 | 1.076 ± 0.20[**$$] | 623.1 ± 27.9[##$$] |

[#]$P < 0.05$,
[##]$P < 0.01$, in comparison with the model control group;
[*]$P < 0.05$,
[**]$P < 0.01$, in comparison with the docetaxel group;
[$]$P < 0.05$,
[$$]$P < 0.01$, in comparison with the Tegafur, Gimeracil and Oteracil Potassium Capsules group.

From the experiment showing the effect of icaritin on bone marrow suppression induced by chemotherapy in tumor-bearing mice in the present Example (Table 2), it was found that in comparison with the model group, the number of neutrophils in the mice in the docetaxel group or the Tegafur, Gimeracil and Oteracil Potassium Capsules group was significantly reduced, while icaritin had an unexpected effect of alleviating bone marrow suppression. Specifically, in comparison with the model group, the total number of white blood cells, the number of platelets and the number of neutrophils in the icaritin group all increased with very significant difference ($P<0.01$) or with significant difference

EXAMPLE 23

Effect of Icaritin on the Number of Blood Cells in Mice Receiving $^{60}$Co Radiation 1. Materials 1.1 Test animals: Kunming mice (purchased from Chinese National Institute for the Control of Pharmaceutical and Biological Products, License of Laboratory Animal No.: SCXK II-00-0010), half male and half female, 7 weeks old, 18-22 g, test temperature (20±1) ° C., humidity 40%~70%, free access to water, normal feeding.

1.2 Test reagents:

| Test reagents | Manufacturers or sources |
|---|---|
| Icaritin Microemulsion Formulation | Prepared according to the process of Example 1, purity of icaritin: 99.3% |
| Epimedium Extract | Prepared in-house, the process of extraction was described below in the Method section |

2. Method:

Mice in each group, except for the normal group (10 mice), were radiated with 4 Gy of $^{60}$Co by one-time systemic radiation with an absorbed dose of 4 Gy and an absorbed dose rate of 0.88 Gy/min. Blood was sampled at days 3, 7 and 10 after the radiation, respectively, from orbital vein for the whole blood cell count. The mice of which the number of white blood cells was lower than $3.0 \times 10^9$/L or the number of platelets was lower than $500 \times 10^9$/L in two consecutive whole blood cell counts were excluded, and the remaining mice were used to be tested.

The mice which met the requirements of the experiment after the radiation were randomly divided into the following model control group, epimedium extract group and icaritin group, with 10 animals in each group and half male and half female. Each group was treated or administered as follows.

Group 1, the normal group: administered by intraperitoneal injection with 0.9% normal saline in an administration volume of 10 ml/kg;

Group 2, the model control group: administered by intraperitoneal injection with 0.9% normal saline in an administration volume of 10 ml/kg;

Group 3, the epimedium extract group: administered by intraperitoneal injection with 3.5 ml/kg/d of aqueous extract of epimedium;

Group 4, the icaritin group: administered by intraperitoneal injection with 10 mg/kg/d of icaritin with an administration volume of 10 ml/kg;

The process for preparing the epimedium extract was as follows: (1) putting epimedium into a pot, adding fresh water to immerse the drug; (2) soaking for 30 min so that the active ingredients in the epimedium were easily decocted out; (3) quickly heating to sufficient boiling for 1-3 min, then continuing to heat for 20-30 min to concentrate the liquid, and filtering the liquid into a cup through sterile gauze; (4) decocting the drug well in one time, and mixing the first dose with the second dose well in order to balance the potency of the drug. 200 mL of aqueous extract was prepared from 1 kg of epimedium. The epimedium extracts employed in the following experiments were all prepared by this process.

Each group was administered once a day for totally 10 days. During the test, the animals were observed for their food and water uptake, survival conditions and behaviors every day, and measured for their body weights every day. After the test was ended, blood was sampled from abdominal aorta for routine blood test, and the total number of white blood cells and the total number of platelets were determined.

3. Experimental results:

TABLE 3

Effect of icaritin on the white blood cells and platelets in mice receiving 4 Gy of $^{60}$Co radiation

| Groups | Sample n. | White blood cells ($10^9$/L) | Platelets ($10^9$/L) |
|---|---|---|---|
| Normal Group | 10 | 4.926 ± 0.50 | 678.2 ± 78.5 |
| Model Control Group | 10 | 2.535 ± 0.38 | 482.0 ± 54.2 |
| Epimedium Extract Group | 10 | 3.242 ± 0.45 | 524.5 ± 74.6 |
| Icaritin Group | 10 | 4.225 ± 0.51[##$] | 596.2 ± 72.5[#$] |

[#]$p < 0.05$,
[##]$p < 0.01$, in comparison with the model control group;
[$]$p < 0.05$, in comparison with the epimedium extract group.

Through the experiment showing the effect of icaritin on the white blood cells and the platelets in mice receiving 4 Gy of $^{60}$Co radiation in the present Example (Table 3), it was found that icaritin had an unexpected effect of alleviating bone marrow suppression induced by radiation therapy. Specifically, the total number of white blood cells and the total number of platelets in the icaritin group both increased with very significant difference ($P<0.01$) or with significant difference ($P<0.05$) in comparison with the model group; and with significant difference ($P<0.05$) in comparison with the epimedium extract group.

EXAMPLE 24

Effect of Icaritin on the White Blood Cells and Platelets in NOD Mice

Non-obese diabetic (NOD) mice are a large mouse strains, including NOD/Scid, NOD/Ltj mice, etc. The NOD/Ltj mice used in this experiment are mice with an abnormal immune system in which platelets and white blood cells are obviously lower than those in normal mice.

1. Materials 1.1 Test animals: NOD/Ltj mice (purchased from Beijing Vital River Laboratory Animal Technology Co., Ltd., License of Laboratory Animal No.: SCXK (Jing) 2006-0009); female; 5 weeks old; 16-20 g, 52 mice.

1.2 Test reagents:

Interleukin, purchased from Beijing Sino Biological Inc.

Pentobarbital sodium, purchase from Shanghai Kefeng Chemical Reagents Co., Ltd.

Icaritin, prepared according to the process of Example 1, purity of icaritin: 99.3%.

2. Grouping and Marking:

5-Week-old healthy NOD mice, after adaptive feeding for one week, were randomly divided into 4 groups:

Group I was the blank control group, totally 13 mice; and was administered intragastrically with normal saline in the same volume of interleukin daily;

Group II was the positive control group, totally 13 mice, and was administered intragastrically with 10.0 mg/kg of interleukin daily;

Group III was the low-dose icaritin group, totally 13 mice, and was administered intragastrically with 30 mg/kg of icaritin daily;

Group IV was the high-dose icaritin group, totally 13 mice, and was administered intragastrically with 60 mg/kg of icaritin daily.

Each group was administered once a day for consecutively 15 days. The mice were anaesthetized (with 3% pentobarbital sodium, by intraperitoneal injection, at 0.1-0.15 ml per animal). 1 ml of blood wass sampled from abdominal aorta into an anticoagulation tube for routine blood test.

TABLE 4

Effect of icaritin on the white blood cells and platelets in NOD mice

| Groups | Sample n. | White blood cells ($10^9$/L) | Platelets ($10^9$/L) |
|---|---|---|---|
| Blank Control Group | 13 | 2.535 ± 0.38 | 508.3 ± 38.6 |
| Interleukin Group | 13 | 2.683 ± 0.35 | 524.5 ± 74.6 |
| Low-Dose Icaritin Group | 13 | 3.242 ± 0.45 #$ | 730.5 ± 34.6##$ |
| High-Dose Icaritin Group | 13 | 4.225 ± 0.51##$ | 780.2 ± 46.5 ##$$ |

$p < 0.05$,
$p < 0.01$, in comparison with the blank control group;
$$p < 0.01$,
$$$p < 0.01$, in comparison with the interleukin group.

It can be seen from Table 4 that the number of white blood cells and the number of platelets in the high-dose icaritin group and the low-dose icaritin group were both significantly higher than those in the model group, indicating a significant therapeutic effect. In comparison with the anti-thrombocytopenia positive control interleukin, icaritin not only had significant advantage in increasing the number of white blood cells ($p<0.05$), but also significantly increased the number of platelets, improving the immunocompetence of the body, especially for the high-dose icaritin group, which showed a very significant advantage in increasing white blood cells and platelets in comparison with the other groups.

EXAMPLE 25

Effect of Icaritin on the Bleeding Time and Clotting Time in Normal Mice 25.1 Test Animals and Test Drugs:

Kunming mice, half male and half female, body weight 20±2.0 g; Wistar rats, body weight 200±20 g, half male and half female. Test animals were provided by New Drug Pharmacological Center of Shandong Xinshidai Medicine Industry Co., Ltd.

Test drugs: icaritin, prepared according to Example 1; icariin, prepared by the method of Example 1 in CN101607976B, with a purity of 98%. Icariin employed in the following Examples was prepared in the same way as in this example.

25.2. Grouping and Administration

100 Kunming mice were randomly divided into 5 groups, i.e. the blank control group (normal saline group), the icariin group (positive control group), the high-dose icaritin group, the medium-dose icaritin group, and the low-dose icaritin group. Each group was administered as follows.

Blank control group: administered with the same volume of normal saline by subcutaneous injection;

Icariin group: administered with 2 mg/kg of icariin by injection;

High-dose icaritin group: administered with the injection of icaritin of Example 1 by subcutaneous injection at a dosage of 10 mg/kg;

Medium-dose icaritin group: administered with the injection of icaritin of Example 1 by subcutaneous injection at a dosage of 5 mg/kg;

Low-dose icaritin group: administered with the injection of icaritin of Example 1 by subcutaneous injection at a dosage of 1 mg/kg.

25.3 Measurements of the bleeding time and the clotting time

Measurement of the bleeding time: The normal saline group (blank control group), the icariin group (positive control group), and the icaritin administration groups (high-, medium-, and low-dose groups) were designed as follows: 50 mice were selected, weighed, and randomly divided into 5 groups, with 10 mice in each group. The animals were administered consecutively for 3 days. At 1 h after the last administration, a filter paper was rolled to form a filter paper cartridge with a diameter similar to that of the mouse body, which was closed at one end. The mouse was allowed to climb into the cartridge. Then about 3 mm of tail tip of the mouse was cut with scissors. A stopwatch was started to record the time when the bleeding started. The tail tip of the mouse was point-contacted with a filter paper gently every 15 s until there was no blood or no blood can be seen. The recorded time was the bleeding time, and the results were shown in Table 5.

Measurement of the clotting time: The normal saline group (blank control group), the icariin group (positive control group), and the icaritin administration groups (high-, medium-, and low-dose groups) were designed as follows: 50 mice were selected, weighed and randomly divided into 5 groups, with 10 mice in each group. The animals were administered consecutively for 3 days. At 1 h after the last administration, blood was sampled from the venous plexus by inserting a disposable 20 µl blood collection tube into the inner canthus of the mouse to collect 20 µl of blood. A small fragment of capillary was broken off every 15 s for checking the occurrence of clotting filaments. The time from the blood sampling to the occurrence of fibrous protein filaments (clotting time) was recorded, and the results were shown in Table 5.

TABLE 5

Measurement results of the bleeding time and the clotting time

| Groups | n | Dosage | Bleeding Time | Clotting Time |
|---|---|---|---|---|
| Blank Control Group | 10 | — | 5.11 ± 0.62 | 5.68 ± 0.72 |
| Icariin Group | 10 | 2 mg/kg | 4.03 ± 0.45* | 4.28 ± 0.61* |
| High-Dose Icaritin Group | 10 | 10 mg/kg | 1.86 ± 0.24**$^{\Delta\Delta}$ | 1.96 ± 0.16**$^{\Delta\Delta}$ |
| Medium-Dose Icaritin Group | 10 | 5 mg/kg | 2.51 ± 0.35**$^{\Delta}$ | 3.04 ± 0.31**$^{\Delta}$ |
| Low-Dose Icaritin Group | 10 | 1 mg/kg | 3.75 ± 0.46* | 3.84 ± 0.55* |

Note:
*P < 0.05,
**P < 0.01, in comparison with the blank control group;
$^{\Delta}$P < 0.05,
$^{\Delta\Delta}$P < 0.01, in comparison with the icariin group.

As can be seen from Table 5, the icaritin administration groups and the icariin group all showed reduction in the bleeding time and the clotting time in normal mice, in which each of the icaritin administration groups was superior to the icariin group in decreasing the bleeding time and the clotting time in normal mice, and icaritin showed dose dependence in reducing the bleeding time and the clotting time in normal mice, and the high-dose icaritin group and the medium-dose icaritin group showed significant difference in comparison with the icariin group.

EXAMPLE 26

Effect of Icaritin on the Number of the Platelets in the ITP Model 26.1 Model preparation, grouping and administration Establishment of chronic ITP model: Wistar rats were selected to establish the model by injecting rabbit anti-rat platelet serum (APS). The rat was intraperitoneally injected with 1:4 diluted APS (0.7 ml/200 g body weight) for consecutively 3 days, which can significantly reduce the number of platelets. 50 Rats in which the model was successfully established were selected, weighed, and randomly divided into 5 groups, i.e. the model control group, the icariin group (positive control group), and the icaritin administration groups (high-, medium- and low-dose groups), with 10 rats in each group. The groups were administered with the following therapeutic agents, respectively.

The model control group: administered by subcutaneous injection with the same volume of normal saline;

The icariin group: administered by subcutaneous injection with 2 mg/kg of icariin;

The high-dose icaritin group: administered by subcutaneous injection with 10 mg/kg of the icaritin injection of Example 11;

The medium-dose icaritin group: administered by subcutaneous injection with 5 mg/kg of the icaritin injection of Example 11;

The low-dose icaritin group: administered by subcutaneous injection with 1 mg/kg of the icaritin injection of Example 11.

26.2 Platelet counts in rats of the administration groups

At 1 h after the last administration, blood was sampled from the venous plexus by inserting a disposable 20 μl blood collection tube into the inner canthus of the mouse. The total number of platelets in the rat was determined, and the results were shown in table 6.

TABLE 6

Results of the platelet count in each group of rats

| Groups | n | Dosage | Platelet count (×10$^9$) |
|---|---|---|---|
| Model Control Group | 10 | — | 423.6 ± 52.4 |
| Icariin Group | 10 | 2 mg/kg | 571.8 ± 60.6* |
| High-Dose Icaritin Group | 10 | 10 mg/kg | 819.96 ± 61.8**$^{\Delta\Delta}$ |
| Medium-Dose Icaritin Group | 10 | 5 mg/kg | 720.4 ± 60.3**$^{\Delta}$ |
| Low-Dose Icaritin Group | 10 | 1 mg/kg | 680.84 ± 50.5* |

Note:
*P < 0.05,
**P < 0.01, in comparison with the model control group;
$^{\Delta}$P < 0.05,
$^{\Delta\Delta}$P < 0.01, in comparison with the icariin group.

As can be seen from Table 6, the icaritin administration groups and the icariin group all can increase the number of platelets in ITP rats, in which each of the icaritin administration groups was superior to the icariin group in increasing the number of platelets in ITP rats, icaritin showed dose dependence in increasing the number of platelets in ITP rats, and the high-dose icaritin group and the medium-dose icaritin group showed significant difference in comparison with the icariin group.

In summary, icaritin can show a positive therapeutic effect on the chronic ITP model rats, and was superior to the positive control, icariin, in decreasing the thrombin time, prothrombin time and partial thromboplastin time, and increasing the number of platelets in the chronic ITP model rats. The high- and medium-dose groups can significantly shorten the thrombin time (TT), prothrombin time (PT) and partial thromboplastin time (APTT) in the chronic ITP model rats (P<0.05), and had a very significant effect in increasing the number of platelets in the rats (P<0.01). Accordingly, the traditional Chinese medicine composition of the present application can be used to treat thrombocytopenia, especially to treat immune thrombocytopenia.

EXAMPLE 27

Effect of Icaritin on the Active Immune Thrombocytopenia in Mice 27.1 Model preparation, grouping and administration 72 Balb/C mice were selected, weighed, and randomly divided into 5 administration groups, i.e. the normal group, the model control group, the icariin group (positive control group), and the icaritin administration groups (high-, medium-, and low-dose groups), with 12 mice in each group. Balb/C mice in each group except for the normal group were intraperitoneally injected with platelets of SD rats once a week for consecutively three times, which may significantly reduce the number of platelets. On the second day after the model was established, each group was administered with the following therapeutic agents:

The normal group: administered intragastrically with the same volume of normal saline;

The model control group: administered intragastrically with the same volume of normal saline;

The icaritin group: administered intragastrically with 20 mg/kg of icariin;

The high-dose icaritin group: administered intragastrically with 100 mg/kg of the icaritin tablets of Example 9;

The medium-dose icaritin group: administered intragastrically with 50 mg/kg of the icaritin tablets of Example 9;

The low-dose icaritin group: administered intragastrically with 10 mg/kg of the icaritin tablets of Example 9.

Each of the administration groups was administered once a day and fed normally. After establishing the model three times, each administration group was continued to be administered for one week. The mice were anesthetized, and blood was sampled to measure the number of platelets and determine the effect of icaritin on the number of platelets (PLT) in the peripheral blood.

27.2 Experimental results

The results for determining the effect of icaritin on the number of platelets (PLT) in the peripheral blood were shown in Table 7.

TABLE 7

Effect of icaritin on active immune thrombocytopenia in mice

| Groups | n | Dosages | PLT ($10^9$/L, x ± s) |
|---|---|---|---|
| Normal Control Group | 12 | — | 1213.6 ± 107.6 |
| Model Control Group | 12 | — | 603.3 ± 72.1# |
| Icariin Group | 12 | 2 mg/kg | 850.6 ± 90.1** |
| High-Dose Icaritin Group | 12 | 100 mg/kg | 1193.4 ± 95.4 |
| Medium-Dose Icaritin Group | 12 | 50 mg/kg | 983.5 ± 85.7 |
| Low-Dose Icaritin Group | 12 | 10 mg/kg | 862.7 ± 75.6 |

$p < 0.05$ in comparison with the normal control group;
**$p < 0.01$ in comparison with the model control group.

As can be seen from Table 7, the icaritin administration groups and the icariin group both showed positive therapeutic effects on the active immune thrombocytopenia in mice, and can increase the number of platelets in the active immune thrombocytopenia mice, wherein each of the icaritin administration groups was superior to the icariin group in increasing the number of platelets in the model of active immune thrombocytopenia in mice, icaritin showed dose dependence in increasing the number of platelets in the mouse model of active immune thrombocytopenia, and the high-dose icaritin group and the medium-dose icaritin group showed significant difference in comparison with the icariin group.

EXAMPLE 28

Effect of Icaritin on Thrombocytopenia Induced by Cyclophosphamide in Mice

72 Balb/C mice were selected, weighed, and randomly divided into 6 groups, i.e. the normal group, the model control group, the icariin group (positive control group), and the icaritin administration groups (high-, medium-, and low-dose groups), with 12 mice in each group. The mice were intraperitoneally injected with 50 mg/kg of cyclophosphamide every day for consecutively one week, which can significantly reduce the number of platelets. One week before starting to establish the model, each group was administered with the following therapeutic agents:

The normal group: administered subcutaneously with the same volume of normal saline;

The model control group: administered subcutaneously with the same volume of normal saline;

The icariin group: administered by subcutaneous injection with 2 mg/kg of icariin;

The high-dose icaritin group: administered by subcutaneous injection with 10 mg/kg of the icaritin injection of Example 11;

The medium-dose icaritin group: administered by subcutaneous injection with 5 mg/kg of the icaritin injection of Example 11;

The low-dose icaritin group: administered by subcutaneous injection with 1 mg/kg of the icaritin injection of Example 11.

Each group was administered once a day and fed normally. After consecutive administration for 3 weeks, the mice were anesthetized, and blood was sampled to measure the number of platelets and determine the effect of icaritin on the number of platelets (PLT) in the peripheral blood. The results were shown in Table 8.

TABLE 8

Effect of icaritin on thrombocytopenia induced by cyclophosphamide in mice

| Groups | n | Dosages | PLT ($10^9$/L, x ± s) |
|---|---|---|---|
| Normal Control Group | 12 | — | 1113.6 ± 107.6 |
| Model Control Group | 12 | — | 303.3 ± 72.1# |
| Icariin Group | 12 | 2 mg/kg | 550.6 ± 90.1** |
| High-Dose Icaritin Group | 12 | 10 mg/kg | 894.6.4 ± 82.4 |
| Medium-Dose Icaritin Group | 12 | 5 mg/kg | 725.9 ± 66.7 |
| Low-Dose Icaritin Group | 12 | 1 mg/kg | 633.5 ± 43.2 |

$p < 0.05$ in comparison with the normal control group;
**$p < 0.01$ in comparison with the model control group.

As can be seen from Table 8, the icaritin administration groups and the icariin group showed a positive therapeutic effect on thrombocytopenia induced by cyclophosphamide in mice, and can increase the number of platelets in the model of thrombocytopenia induced by cyclophosphamide in mice, wherein each of the icaritin administration groups was superior to the icariin group in increasing the number of platelets in the model of thrombocytopenia induced by cyclophosphamide in mice, and icaritin showed dose dependence in increasing the number of platelets in the model of thrombocytopenia induced by cyclophosphamide in mice, and the high-dose icaritin group and the medium-dose icaritin group showed significant difference in comparison with the icariin group.

All the publications mentioned in the above description are incorporated herein by reference. Although the present application has been described with reference to specific preferred embodiments, it should be understood that the claimed invention is not limited to the specific embodiments. Virtually, various modifications of the described modes for implementing the present application will be apparent for a skilled person in biochemistry and bioengineering or relevant fields, and should be within the scope of the appended claims of the present application.

The invention claimed is:

1. A method for treating thrombocytopenia comprising administering a composition comprising an effective amount of icaritin as the sole active ingredient to a human suffering from thrombocytopenia.

2. The method according to claim 1, wherein the thrombocytopenia is immune thrombocytopenia or secondary thrombocytopenia.

3. The method according to claim 2, wherein the immune thrombocytopenia is chronic idiopathic thrombocytopenic purpura.

4. The method according to claim 2, wherein the secondary thrombocytopenia is induced by bone marrow suppression caused by a radiation or a chemical drug.

5. The method according to claim 4, wherein the chemical drug is docetaxel, cyclophosphamide, or S-1.

6. The method according to claim 1, wherein icaritin is administered in the form of an oral formulation or a formulation for parenteral administration.

7. The method according to claim 6, wherein the formulation for parenteral administration is an injection.

8. The method according to claim 6, wherein the oral formulation is a tablet, granule or capsule.

9. The method according to claim 6, wherein the oral formulation or the injection contains icaritin in an amount of 0.1 to 500 mg per unit dosage.

10. The method according to claim 1, wherein icaritin is orally administered to human at a dosage of 0.1 mg/kg/d - 100 mg/kg/d.

11. The method according to claim 1, wherein icaritin is administered to human by injection at a dosage of 0.01 mg/kg - 10 mg/kg.

12. The method according to claim 1, wherein icaritin is administered in the form of solid, liquid, oil, emulsion, gel, aerosol, inhalant, spray, capsule, pill, patch, or suppository.

* * * * *